United States Patent [19]

Elliott et al.

[11] Patent Number: 4,789,754

[45] Date of Patent: Dec. 6, 1988

[54] PESTICIDE INTERMEDIATES

[75] Inventors: Michael Elliott, Stevenage; Norman F. Janes, Luton; Richard L. Elliott, Great Bookham; Bhupinder P. S. Khambay, Harrow Weald; David A. Pulman, Caddington, all of England

[73] Assignee: National Research Development Corporation, London, England

[21] Appl. No.: 849,070

[22] Filed: Apr. 7, 1986

Related U.S. Application Data

[62] Division of Ser. No. 517,393, Jul. 26, 1983, Pat. No. 4,594,355.

[30] Foreign Application Priority Data

Jul. 29, 1982 [GB] United Kingdom ................ 8221860

[51] Int. Cl.$^4$ ............................................. C07C 121/52
[52] U.S. Cl. ...................................... 558/388; 568/715
[58] Field of Search ........................ 558/388; 568/715

[56] References Cited

PUBLICATIONS

Elliott et al., "Chem. Abst." vol. 68 (1968) 49262e and 8th Coll. Index p. 4686S.
Elliott et al.–Nature, vol. 207, No. 5,000, pp. 938–940–Aug. 28th 1965.

*Primary Examiner*—Anton H Sutto
*Attorney, Agent, or Firm*—Oblon, Fisher, Spivak, McClelland & Maier

[57] ABSTRACT

A compound of the formula:

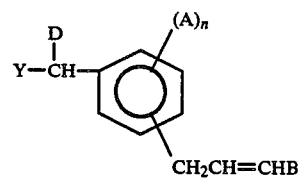

wherein
Y represents OH or a halogeno group;
D represents hydrogen or a cyano group;
B represents hydrogen or a methyl, ethyl or vinyl group;
A represents methyl;
n is 0, 1 or 2;
with the proviso that
(1) when the $CH_2CH=CHB$ group is in the 4-position with respect to the CHDY group, then D must be hydrogen and B must be methyl, ethyl or vinyl and the configuration about the double bond in the $CH=CHB$ group must be Z and
(2) when the group $CH=CHB$ is in the 3-position with respect to the CHDY group and D is CN then n must be 0 and
(3) when the group $CH_2CH=CHB$ is in the 2 or 3-position with respect to the CHDY group, then D is CN, are useful in the production of pesticidal esters of chrysanthemic and related acids.

6 Claims, No Drawings

PESTICIDE INTERMEDIATES

This is a division, of application Ser. No. 517,393, filed July 26, 1983, now U.S. Pat. No. 4,594,355.

This invention relates to pesticides and in particular to pesticidal compounds, the preparation of such compounds, intermediates for use in their prepraration, compositions containing such compounds and the use of such compounds and compositions to control pests, for example pests present in soil.

Accordingly the present invention comprises a compound of formula I

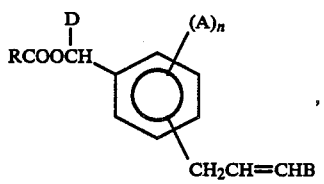

in which formula:
- D represents hydrogen or a cyano group or an ethynyl group;
- B represents hydrogen, alkyl or alkenyl;
- A represents an alkyl group (typically a $C_1$–$C_6$ alkyl group) or a halogeno group e.g. F, Cl or Br or a $CF_3$ group;
- n is 0 to 4;
- RCOO represents a residue of a 2,2-dimethylcyclopropane carboxylic acid carrying at the 3-position a dihalovinyl, alkenyl or carboalkoxyalkenyl group;
- provided that (1) when the group —$CH_2CH$=$CHB$ is located at the four position in the ring with respect to the ester linkage, then D must be hydrogen and the group carried at the 3-position on the cyclopropane ring of the acid must be a dihalovinyl group and (2) when the group —$CH_2CH$=$CHB$ is located at the 3-position in the ring and D represents a cyano group, then n must be 0.

When the group at the 3-position of the cyclopropane ring is alkenyl or carboalkoxyalkenyl, the alkenyl is an alkmonoenyl, usually branch chained such as isobutenyl or 2-methoxycarbonylpropenyl so that the preferred acid residue of this type is of chrysanthemic acid, especially when in the trans form and particularly when in the (IR,trans) form or pyrethric acid. The most preferred acids are 2,2-dimethyl-3-(2,2-dihalovinyl)-cyclopropane carboxylic acids, the 2,2-dimethyl-3-(2,2-dibromovinyl)-cyclopropane carboxylic acid, especially when in the (IR,cis) form being of particular interest.

When B represent an alkyl or alkenyl group the configuration about the the double bond of the substituent —$CH_2CH$=$CHB$ can be E or Z and compounds in which the configuration is Z are preferred as also are mixtures of geometrical isomers in which the Z isomer predominates. Compounds in which B represents methyl, ethyl or vinyl, are of particular interest, the latter especially so. The preferred position in the ring with respect to the ester linkage for the substituent —$CH_2CH$=$CHB$ is 3 or 4, the 3 position in compounds wherein D represents a cyano group being of particular interest.

The group A, when present, is typically disposed at the 2 position in the ring with respect to the ester linkage and if alkyl, generally represents methyl. Two groups, e.g. methyl, groups, when present, are usually disposed at the 2,6 position in the ring with respect to the ester link. Such compounds are of special interest when B in the group —$CH_2CH$=$CHB$ represents hydrogen, the group preferably being located at the 3 or 4 position in the ring.

As hereinbefore described, esters I of a 2,2-dimethyl-3-(dihalovinyl)-cyclopropane carboyxlic acid, typically an acid in which both halogens, whether fluorine, chlorine or bromine are identical, are preferred and esters of 2,2-dimethyl-3-(dibromovinyl)-cyclopropane carboxylic acid especially so. The following esters of the latter acid, especially when in the (IR cis) form are of particular interest: α-cyano-3-allyl-benzyl(D=CN, B=H); α-cyano-3-methylallyl benzyl (D=CN, B=$CH_3$); 3-methylallyl benzyl (D=H, B=$CH_3$); 3-pentadienyl- and 4-pentadienyl benzyl (D=H, B=—CH=$CH_2$); α-cyano-3-pentadienyl benzyl), α-cyano-3-ethylallyl benzyl (D=CN, B=—$CH_2CH_3$) 2-methyl-3-allylbenzyl (D=H, B=H, A=$CH_3$ n=1); 2,6-dimethyl-4-allyl-benzyl (D=H, B=H, A=$CH_3$, n=2) it being highly preferred that the latter compounds, where possible, exist in the Z configuration.

Esters I may be prepared by reaction of an acid RCOOH or an ester-forming derivative thereof with an intermediate of formula II

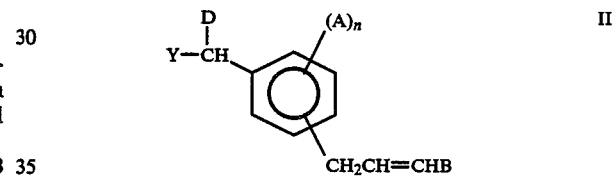

wherein Y represents a hydroxyl or halogen e.g. chlorine, and D, A, n and B are as defined above.

Intermediates of formula II, are also included in a further aspect of the present invention, provided that (1) when the group —$CH_2CH$=$CHB$ is disposed at the 4 position in the ring with respect to the —CHDY group then D must be hydrogen and B must be alkyl or alkenyl and the configuration about the double bond in the group must be Z, and provided that (2) when the group —$CH_2CH$=$CHB$ is disposed at the 3 position with respect to the CHDY group and D represents a cyano group, then n must be 0.

It is generally preferred for the configuration about the double bond in intermediates II to be Z and the following compounds are of particular interest:

(a) II, D=H, n=0, B=—CH=$CH_2$, Z isomer, ring position 3

(b) II, D=H, n=0, B=—CH=$CH_2$, E isomer ring position 3

(c) II, D=CN, n=0, B=—CH=$CH_2$, Z isomer, ring position 3

(d) II, D=H, n=0, B=—CH=$CH_2$, Z isomer, ring position 4

(e) II, D=H, n=0, B=—$CH_3$, Z isomer, ring position 3

(f) II, D=CN, n=0, B=—$CH_3$, Z isomer, ring position 3

(g) II, D=CN, B=—$CH_2CH_3$, Z isomer, ring position 3

(h) D=H, n=1, A=$CH_3$ at ring position 2, B=H at ring position 3. In the latter compounds Y typically represents a hydroxyl group.

The production of intermediates of formula II in which n=O is illustrated by the following reaction schemes. Intermediates where n=1–4 are obtainable starting from the appropriately ring substituted reactant.
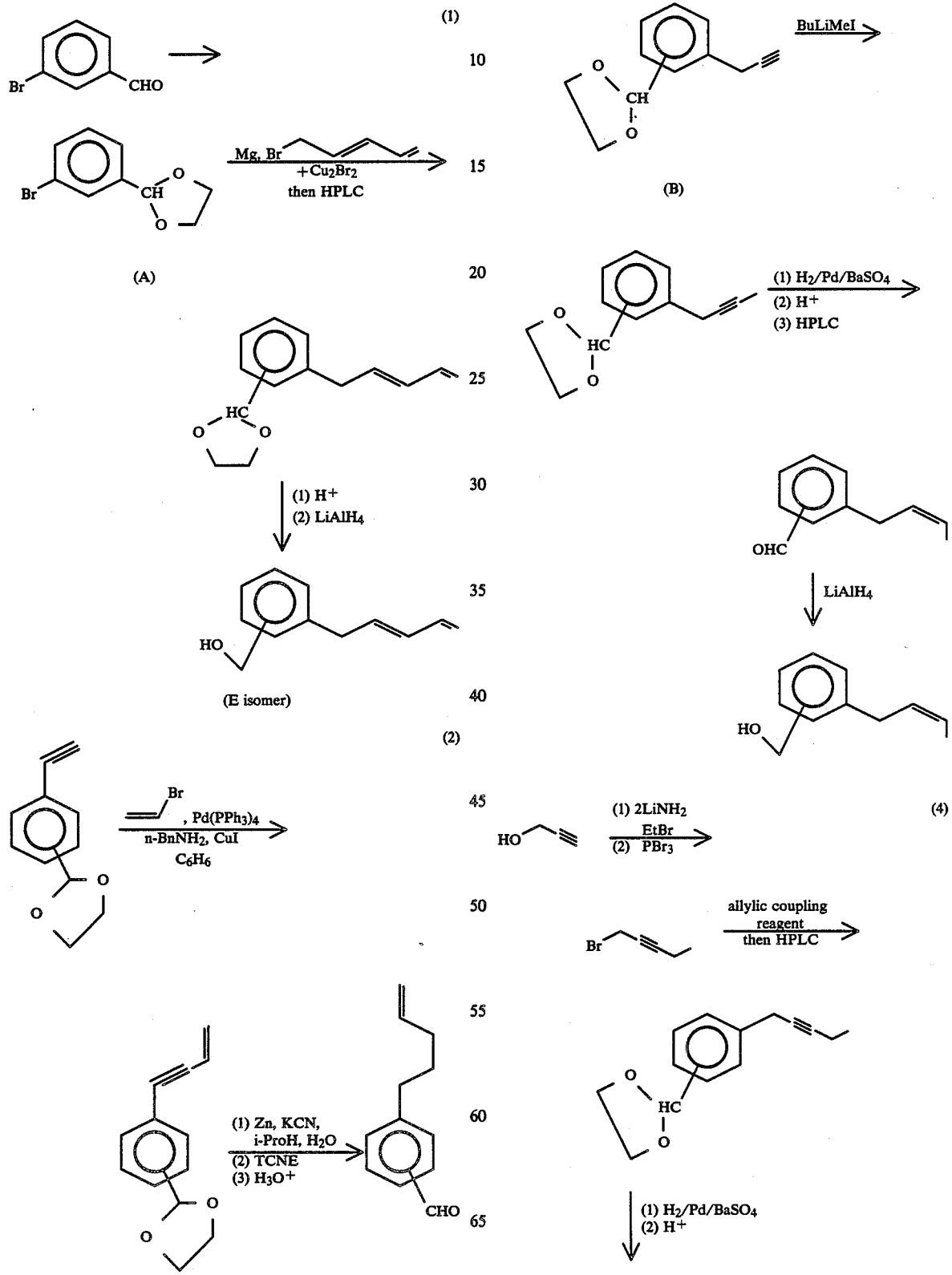

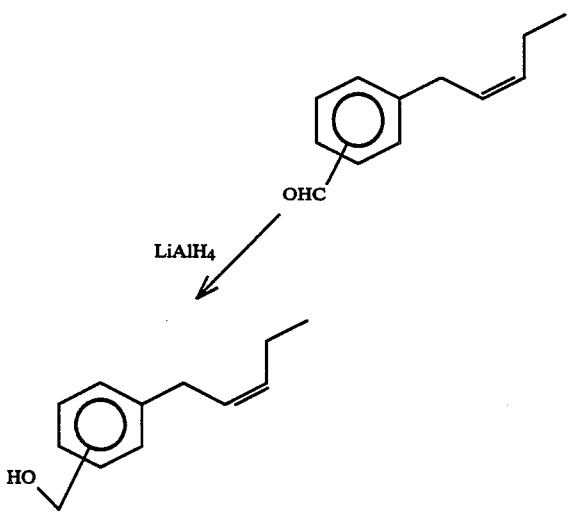

Intermediate cyanohydrins or ethynyl compounds (II, Y=OH, D=CN or C≡CH) are generally produced from the corresponding aldehydes by treatment thereof with an alkali metal cyanide suitably under acid conditions or using a magnesium acetylide. The required aldehydes are usually obtained by pyridinium dichromate oxidation of the corresponding alcohols produced by methods analogous to those shown in the schemes above.

Intermediates II in which Y represents halogen and D represents hydrogen may be produced from intermediates II in which Y represents -OH and D represents hydrogen, in accordance with a further aspect of the present invention by treatment of the latter intermediates with a halogenating reagent of the class employed for conversion of carboxylic acids to acyl halides e.g. $SO(hal)_2$, typically with pyridine or $P(hal)_3$, hal representing chlorine or bromine.

As hereinbefore described the compounds of the present invention can be prepared by an esterification involving the reaction of an alcohol of formula II or an esterifiable derivative thereof with a carboxylic acid of formula RCOOH or an esterifiable derivative thereof. It is usually convenient in practice to react an alcohol of formula II with an acyl chloride of formula RCOCl or to react a salt of the carboxylic acid e.g. a silver or triethylammonium salt with a benzylhalide derivative, or cyanobenzyl halide which may be ring alkylated or to esterify the carboxylic acid with the alcohol in the presence of N,N-dicyclohexylcarbodiimide and a catalyst.

Alternatively, the esters of the invention can be prepared by transesterification by reacting a $C_1$-$C_6$ alkyl ester of the carboxylic acid with a benzyl alcohol of formula II in the presence of a basic transesterification catalyst. This method is not usually satisfactory where either molecule contains another base-sensitive residue, e.g. where the carboxylic acid is pyrethric acid.

The compounds of the invention exhibit optical isomerism in that the carbon atom bearing the substituent D can exist in the R or S configuration and the present invention includes compounds in which the configuration is substantially completely R or in which the configuration is substantially completely S or mixtures thereof.

Compounds of the invention can exist in the form of both geometrical and optical isomers. This is because of the unsymmetrical substitution at $C_1$ and $C_3$ of the cyclopropane ring. Compounds of the present invention include those isomers in which the hydrogen atoms at $C_1$ and $C_3$ of the cyclopropane ring are substantially completely in the cis configuration or substantially completely in the trans configuration or mixtures thereof. The present invention also includes compounds in which the configuration at $C_1$ is substantially completely R or substantially completely S and mixtures thereof. In the compounds of the invention the optical configuration at $C_1$ and $C_3$ cannot very independently of the geometrical configuration of the hydrogen atoms at $C_1$ and $C_3$ of the cyclopropane ring. The effect of this is that the configuration of the cyclopropane ring can be defined uniquely by specifying the optical configuration at $C_1$ and the geometrical configuration of the hydrogen atoms at $C_1$ and $C_3$ and, for definition purposes, we have adopted nomenclature of the form (1R)-cis, (1R)-trans etc. it being unnecessary to specify the optical configuration at $C_3$ which is fixed once the other two variables are defined. Adopting this nomenclature avoids the confusion which can arise by having to designate either R or S to the same optical configuration at $C_3$ depending upon the nature of the substituents on the cyclopropane ring and even those on the side chain.

When R is a group in which the substitution about the ethylenic bond is asymmetrical, then the configuration of this part of the molecule can be substantially completely in the E form or substantially completely in the Z form or a mixture thereof.

The compounds of the present invention can be in the form of single isomers but, having regard to the fact that the compounds have at least one and frequently more than one centre of asymmetry, the compounds of the invention will normally be in the form of isomer mixtures, although these isomer mixtures can be optically active and/or substantially completely in one geometric form.

One or more of the pesticidal esters of formula I can be formulated with an inert carrier or diluent to give pesticidal compositions and such compositions form a further aspect of the present invention. These compositions can be in the form of dusts and granular solids, wettable powders, mosquito coils and other solid preparations, or as emulsions, emulsifiable concentrates, sprays and aerosols and other liquid preparations after the addition of the appropriate solvents, diluents and surface-active agents.

Compositions formulated in a manner suitable for controlling soil pests typically by treatment of the soild are of especial interest. For this purpose compositions containing compounds I hereinbefore described are particularly suitable as they generally have lower molecular weights than many previously described pyrethroids, and it is envisaged that their relatively high vapour pressures allow them to diffuse through the soil.

The pesticidal compositions of the invention will normally contain from 0.001 to 25% by weight of the compound of formula I but the compositions can contain higher concentrations of active ingredient of formula I e.g. up to 95 % for compositions to be sold as concentrates for dilution before use by the ultimate user.

The compositions of the invention can include diluents such as hydrocarbon oils, e.g. xylene or other petroleum fractions, water, anionic, cationic or non-ionic surface-active agents, anti-oxidants and other stabilisers as well as perfumes and colouring matters. These inert ingredients may be of the type and in proportions such as are conventionally used in pesticidal compositions containing pyrethroid-like compounds.

In addition to these inactive ingredients, the compositions of the present invention may contain one or more further active ingredients which may be other pesticidal compounds of the pyrethroid type or of other types and the composition may also include synergists of the type known to be capable of synergising the activity of natural pyrethrin and pyrethroid-like insecticides. Synergists of this type include piperonyl butoxide, tropital and sesamex.

The compounds of formula I can be used to control pest infestation in the domestic, horticultural or agricultural or medical, including veterinary, areas. The compounds or compositions of the invention can be used to combat pest infestation by tresting pests or surfaces or environments susceptible to pest infestation with effective amounts of the active compounds of formula I or of compositions containing them. For example, they may be used in a domestic environment for spraying rooms to combat infestation with houseflies or other insects, they can be used for treatment of stored dry crops or cereals to combat infestation by insects or other pests, they can be used to spray growing crops, e.g. cotton or rice to combat infestation by common pests and they can be used in a medical or veterinary field, e.g. as a cattle spray to prevent or treat infestation by insects or other pests.

Although, as hereinbefore indicated, they are of particular interest for the disinfestation of soil to control pests such as the onionfly, Delia antiqua, the wheat bulb fly, Delia coarctata the compounds may find application in the control of a wide variety of pests including:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the orthoptera, for example *Blatta orientalis, Periplaneta americana, Leucophaea madarae, Blattela germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example *Reticulitermes spp.;* from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Demalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolius* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aondiiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis supp., Euxoa spp., Feltia spp., *Earia insulana,* Heliothis spp., *Laphygma exigua, Mamestra brassicae, Panolis flammea, Prodenia litura,* Spodoptera spp., *Trichoplusia ni, Carposcapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera positica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolntha, Amphimallon solsti tialis* and *Costelytra zealandica;* from the order of the Hymenoptera, for example Diprion spp., Hoplacampa spp., Lasius spp., *Monomorium pharaonis* and Vespa spp., from the order of the Diptera, for example Aedes spp., Anopheles spp., Culex spp., *Drosophila melanegaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The invention is illustrated by the following Examples.

Temperatures are in °C.

The pesticidal acitivity is assessed against houseflies and mustard beetles by using the following techniques:

HOUSEFLIES (*Musca domestica*)

Female flies are treated on the thorax with a one microlitre drop of insecticide dissolved in acetone. Two replicates of 15 flies are used at each dose rate and 6 dose rates are used per compound under test. After treatment, the flies are maintained at a temperature of 20°±1° and kill is assessed 24 and 48 hours after treatment. $LD_{50}$ is values are calculated in micrograms of insecticide per fly and relative toxicities are calculated from the inverse ratios of the $LD_{50}$ values (ee Sawicki et al, Bulletin of the World Health Organisation, 35, 893, (1966) and Sawicki et al, Entomologia and exp. Appli. 10 253, (1967)).

MUSTARD BEETLES (*Phaedon cochleariae Fab*)

Acetone solutions of the test compound are applied ventrally to adult mustard beetles using a micro drop applicator. The treated insects are maintained for 48 hours after which time kill is assessed. Two replicates of 40 to 50 mustard beetles are used at each dose level and 5 dose levels are used for each compound. Again, $LC_{50}$ values are calculated and relative potencies are calculated from the inverse ratios of $LD_{50}$ (see Elliott et al, J. Sci. Food Agric. 20, 561, (1969)).

Relative potencies are calculated by comparison with 5-benzyl-3-furylmethyl (1R)-trans-chrysanthemate (Bioresmethrin) which is one of the more toxic chrysanthemate esters known to house flies and mustard beetles, it toxicity being about 24 times that of allethrin to houseflies and 65 times that of allethrin to mustard beetles.

The invention is illustrated by the following Examples:

EXAMPLE 1

3-(2E,4-pentadienyl)benzyl(IR)cis-3-(2,2-biromovinyl)2,2-dimethylcyclopropane carboxylate (a)

Grignard reagent from 3-bromobenzaldehyde ethylene acetal

Dry Mg (0.74 g) under dry $N_2$ in a flask is covered with THF (10 ml) and a crystal of $I_2$ added. 5 ml of a solution of 3-bromobenzaldehyde ethylene acetal (7.0 g) in THF (30 ml) is added and kept until it becomes warm, when it is cooled to 15°, and the remainder of the acetal solution added over 15 minutes, then stirred for an additional 1 hour.

(b)

3(2E,4-pentadienyl)benzaldehyde

The Grignard reagent from 3-bromobenzaldehyde ethylene acetal (3.0 g) is added to a mixture of 1-bromo-2E,4-pentadiene (2.2 g), copper (I)bromide (0.02 g) and THF (20 ml) cooled to −20°. This is allowed to warm to 20° with stirring over 1 hour.

The mixture is worked up as usual by addition of ammonium chloride and HPLC yields 0.05 g (22%), $n_D^{20}$ 1.5723.

(c)

3(2E,4-pentadienyl)benzyl alcohol

The aldehyde (0.50 g) in ether is added to lithium aluminum hydride (0.08 g) in ether (20 ml) and the mixture is stirred at 20° for 1 hour. After successive dropwise additions of water (80 μl), 15% NaOH (80 μl) and water 240 μl), the resulting clear ether layer (and washings) is evaporated to a residue of 3-(2E,4-pentadienyl)benzyl alcohol. Yield 0.48 g (95%), $n_d^{20}$ 1.5654.

(d)

3-(2E,4-pentadienyl)benzyl (IR)cis-3-(2,2-dibromovinyl)2,2-dimethylcyclopropane carboxylate The alcohol (0.11 g) in benzene (5 ml) is added to (IR)cis 3-(2,2-dibromovinyl)2,2-dimethylcyclopropanecarbonyl chloride (0.20 g) in benzene (5. ml). Pyridine (0.075 ml) is then added and the mixture is stirred at 20° for 16 hours. This is chromatographed on florisil and the fraction eluted by 7% ether in petrol evaporated to a residue of the title compound (0.20, 70%) $n_D^{20}$ 1.5769.

EXAMPLE 2

3-(2Z,4-pentadienyl)benzyl(IR)cis-3-(2,2-dibromovinyl)2,2-dimethylcyclopropane carboxylate (a)

3(2-propynyl)benzaldehyde ethylene acetal

Dry Mg (0.74 g) under dry $N_2$ in a flask is covered with THF (10 ml) and a crystal $I_2$ added. 5 ml of a solution of 3-bromobenzaldehyde ethylene acetal (7.0 g) in THF (30 ml) is added and kept until it becomes warm, when it is cooled to 15°, and the remainder of the acetal solution added over 15 minutes, then stirred for an additional 1 hour. A mixture of methoxyallene (2.45 g), copper (1)chloride (0.30 g) and THF (30 ml) is cooled to −20°. The above Grignard solution (under moisture excluding conditions) is then added to this solution during 5 minutes, and allowed to warm to 20° with stirring over 30 minutes. Saturated aqueous ammonium chloride is added and the product is extracted with ether. The ether layer is washed with water, dried (MgSO4) and the residue distilled in vacuo. Yield 4.3 g (75%) 89°–96° (0.03 m Hg), $n_D^{20}$ 1.5422.

(b)

3(pent-4-en-2-ynyl)benzaldehyde ethylene acetal

Copper (1) iodide (0.10 g) tetrabistriphenylphosphine palladium (0)(0.60 g) and n-butylamine (1.6 ml) are added to a solution of the acetylenic acetal (2.0 g) in benzene (50 ml) at 10°. Vinyl bromide (5 ml) is added and the mixture stirred at 20° for 16 hours. This is evaporated under reduced pressure, the residue is extracted with carbon tetrachloride and chromatographed on florisil. The fraction eluted by 10% ether in petrol is collected. Yield 1.9 g (83%) $n_D^{20}$ 1.5610.

(c)

3(2Z,4-pentadienyl)benzaldehyde

The enyne acetal (1.9 g) is stirred with zinc powder (75 g), potassium cyanide (6.5 g) in a mixture of n-propanol and water (250 ml, 1:1) at 20° under $N_2$ for 16 hours. This is filtered through celite and the filtrate partitioned between ether and water. The organic layers are washed with saturated aqueous NaCl, and dried (MgSO4). The residue is taken up in benzene (20 ml) and tetracyanoethylene (0.10 g) is added. This is stirred at 20° for 15 minutes, then passed down a florisil column. The fraction eluted by 10% ether in petrol is collected. This residue is hydrolysed by treatment with 3N HCl and the product purified by HPLC. Yield 0.23 g (15%) $n_D^{20}$ 1.5613.

(d)

3(2Z,4-pentadienyl)benzyl alcohol

The aldehyde is reduced to the alcohol with lithium aluminum hydride, following the procedure of Example 1(c).

(e)

3(2Z,4-pentadienyl)benzyl(IR)cis-3-(2,2-dibromovinyl)
2,2-dimethylcyclopropane carboxylate The alcohol is esterified by following the procedure of Example 1(d) to yield the ester, 88%, $n_D^{20}$ 1.5710.

EXAMPLE 3

3-(Z-2-butenyl)benzyl(IR)cis-3-dibromovinyl)2,2-dimethylcyclopropane carboxylate (a)

3(2-butynyl)benzaldehyde

The acetylenic acetal of Example 2(a) (1.5 g) in THF (10 ml) is cooled to −78° under N₂. A mixture of n-butyl lithium (5.1 ml, 1.55 m) (in hexane) and THF (7 ml) is added dropwise over 5 minutes, stirring is continued at −78° for 30 minutes. A mixture of methyl iodide (2.3 g) and THF (4 ml) is then added over 2 minutes and the reaction mixture allowed to warm to 20° with stirring over 1 hour. Saturated aqueous ammonium chloride is added and the organic layer evaporated under reduced pressure to a small residue of 3(Z2-butynyl)-benzaldehyde ethylene acetal. This is dissolved in THF (20 ml) and treated with 3N NCl (10 ml) at 20° for 1 hour. The product is partitioned between ether and water, and the ether layer washed with aq. NaHCO₃, H₂O, dried (MgSO4). The residue is purified by preparative HPLC, yield 1.13 g (90%), $n_D^{20}$ 1.5575.

(b)

3-(Z-2-butenyl)benzaldehyde

The acetylenic acetal of Example 3(a) (0.50 g) is dissolved in pyridine (15 ml). Palladium on Barium Sulphate (0.10 g) is added and the mixture is stirred under an atmosphere of hydrogen until the uptake of H₂ ceases. The mixture is filtered, THF (50 ml) and 3N HCl (150 ml) are added to the filtrate and this is stirred at 20° for 1 hour. The THF is evaporated under reduced pressure and the product is extracted with ether. The ether layer is washed with aq. Na HCO₃, H₂O and dried (MgSO4). The residue is purified by prep. HPLC. Yield 0.20 g (50%), $n_D^{20}$ 1.5389.

(c)

3-(Z-2-butenyl)benzyl alcohol

The aldehyde is reduced to the corresponding alcohol with lithium aluminiun hydride by following the procedure of Example 1(c).

(d)

3-(Z-2-butenyl)benzyl(IR)cis-3-(2,2-dibromovinyl)2,2-dimethylcyclopropane carboxylate The alcohol is esterified by following the procedure of Example 1(d) to yield the ester, 76%, $n_D^{20}$ 1.5627.

EXAMPLE 4

α-cyano 3-(2Z,4-pentadienyl)benzyl(IR)cis-3-(2,2-dibromovinyl)2,2-dimethycyclopropane carboxylate (a)

3(2Z,4-pentadienyl)benzaldehyde cyanohydrin

3(2Z,4-pentadienyl)benzaldehyde produced as described in Example 2(c) (0.23 g) and potassium cyanide (0.40 g) in water (1.0 ml) and THF (4.0 ml) are treated with 40% sulphuric acid (1.2 ml) with cooling to 3°-8°. After 1 hour at 20°, the reaction mixture is extracted with ether, which is washed, dried and evaporated to a residue of 3(2Z,4-pentadienyl)benzaldehyde cyanohydrin (0.25 g, 94%) $n_D^{20}$ 1.5574.

(b)

α-cyano-3(2Z,4-pentadienyl)benzyl(IR)cis-3-(2,2-dibromovinyl)2,2-dimethylcyclopropane carboxylate The cyanohydrin is esterified by following the procedure of Example 1(d) to yield the ester 26% $n_D^{20}$ 1.5639.

EXAMPLES 5 TO 32

Table 1 sets out constants for esters (I) and intermediates (II, Y=OH) produced by following, with appropriate modification, the procedures of Examples 1 to 4 together with bioassay results for esters (I). The esters (I) are produced from intermediates (II) by following the procedure of Example 1(d). Examples 1–4 are also included for ease of reference.

The symbols $B_R$ and $C_R$ respectively represent the acid residues (R):
(IR)cis-2,2-dimethyl-3-(2,2-dibromovinyl)cyclopropane carbonyl and (IR)trans-chrysanthemyl.

TABLE I

COMPOUNDS I AND II

| Ex. No. | D | (A)ₙ | Ring Position | B in —CH₂CH=CHB (isomer) | Ring Position | R(I) | Procedure followed for II(Example) | $n_D^{20}$(I) | $n_D^{20}$(II) or m.p. (°C.) | Relative potencies (Bioresmethrin = 100) HF | MB |
|---|---|---|---|---|---|---|---|---|---|---|---|
| 5 | H | H | — | —CH=CH₂(E) | 3 | $C_R$ | 1 | 1.5362 | 1.5654 | 5 | 0.3 |
| 1 | H | H | — | —CH=CH₂(E) | 3 | $B_R$ | 1 | 1.5679 | 1.5654 | 70 | 5 |
| 6 | CN | H | — | —CH=CH₂(E) | 3 | $C_R$ | 1 + 4 | 1.5338 | 1.5561 | 22 | 6.5 |
| 7 | CN | H | — | —CH=CH₂(E) | 3 | $B_R$ | 1 + 4 | 1.5673 | 1.5561 | 45 | 14 |
| 8 | H | H | — | —CH=CH₂(E) | 4 | $B_R$ | 1 | 1.5764 | 41–41.5 | 51 | 1 |
| 9 | H | H | — | —CH=CH₂(Z) | 3 | $C_R$ | 2 | 1.5355 | 1.5647 | 4 | 0.6 |
| 2 | H | H | — | —CH=CH₂(Z) | 3 | $B_R$ | 2 | 1.5710 | 1.5647 | 90 | 7.3 |
| 10 | CN | H | — | —CH=CH₂(Z) | 3 | $C_R$ | 2 + 4 | 1.5296 | 1.5574 | — | 9 |
| 4 | CN | H | — | —CH=CH₂(Z) | 3 | $C_R$ | 2 + 4 | 1.5639 | 1.5574 | 170 | 14 |
| 11 | H | H | — | —CH=CH₂(Z) | 4 | $B_R$ | 2 | 1.5714 | 1.5647 | 170 | 9 |
| 12 | H | H | — | —CH₃(Z) | 3 | $C_R$ | 3 | 1.5211 | 1.5379 | 2.4 | 1.5 |

TABLE I-continued

COMPOUNDS I AND II

| Ex. No. | D | (A)$_n$ | Ring Position | B in —CH$_2$CH=CHB (isomer) | Ring Position | R(I) | Procedure followed for II(Example) | n$_D^{20}$(I) | n$_D^{20}$(II) or m.p. (°C.) | Relative potencies (Bioresmethrin = 100) HF | MB |
|---|---|---|---|---|---|---|---|---|---|---|---|
| 3 | H | H | — | —CH$_3$(Z) | 3 | B$_R$ | 3 | 1.5627 | 1.5379 | 56 | 10 |
| 13 | CN | H | — | —CH$_3$(Z) | 3 | C$_R$ | 3 + 4 | 1.5143 | 1.5334 | 26 | 17 |
| 14 | CN | H | — | —CH$_3$(Z) | 3 | B$_R$ | 3 + 4 | 1.5507 | 1.5334 | 61 | 52 |
| 15 | H | H | — | —CH$_3$(Z) | 4 | B$_R$ | 3 | 1.5610 | 1.5367 | 30 | 3.0 |
| 16 | H | H | — | —CH$_2$CH$_3$(Z) | 3 | C$_R$ | 3 | 1.5176 | 1.5304 | 0.5 | ca 0.2 |
| 17 | H | H | — | —CH$_2$CH$_3$(Z) | 3 | B$_R$ | 3 | 1.5575 | 1.5309 | 12 | 4 |
| 18 | CN | H | — | —CH$_2$CH$_3$(Z) | 3 | C$_R$ | 3 + 4 | 1.5162 | 1.5292 | 34 | 12 |
| 19 | CN | H | — | —CH$_2$CH$_3$(Z) | 3 | B$_R$ | 3 + 4 | 1.5533 | 1.5292 | 110 | 12 |
| 20 | H | H | — | —CH$_2$CH$_3$(Z) | 4 | B$_R$ | 3 | 1.5540 | 1.5277 | 34 | 3 |
| 21 | H | CH$_3$ | 2 | —CH=CH$_2$(E) | 3 | C$_R$ | 1 | 1.5357 | 1.5680 | 1.8 | 0.6 |
| 22 | H | CH$_3$ | 2 | —CH=CH$_2$(E) | 3 | B$_R$ | 1 | 1.5676 | 1.5680 | 4.5 | 7.7 |
| 23 | H | (CH$_3$)$_2$ | 2,6 | —CH=CH$_2$(E) | 4 | B$_R$ | 1 | 1.5757 | 54–5 | 11 | 4.3 |
| 24 | H | CH$_3$ | 2 | —CH$_2$CH$_3$(Z) | 3 | C$_R$ | 3 | 1.5178 | 1.5370 | 1.4 | 0.7 |
| 25 | H | CH$_3$ | 2 | —CH$_2$CH$_3$(Z) | 3 | B$_R$ | 3 | 1.5573 | 1.5370 | 9.6 | 9.1 |
| 26 | H | CH$_3$ | 2 | H | 3 | C$_R$ | 1 | 1.5219 | 1.5456 | 15 | 3.9 |
| 27 | H | CH$_3$ | 2 | H | 3 | B$_R$ | 1 | 1.5645 | 1.5456 | 120 | 43 |
| 28 | H | (CH$_3$)$_2$ | 2,6 | H | 3 | C$_R$ | 1 | 1.5232 | 1.5441 | 8.5 | 5.2 |
| 29 | H | (CH$_3$)$_2$ | 2,6 | H | 3 | B$_R$ | 1 | 1.5637 | 1.5441 | 45 | 23 |
| 30 | H | (CH$_3$)$_2$ | 2,6 | H | 4 | B$_R$ | 1 | 1.5608 | 1.5434 | 180 | 95 |
| 31 | CN | H | — | H | 3 | C$_R$ | 1 + 4 | 1.5218 | 1.5327 | 18 | 18 |
| 32 | CN | H | — | H | 3 | B$_R$ | 1 + 4 | 1.5549 | 1.5327 | 33 | 44 |

We claim:

1. A compound of the formula:

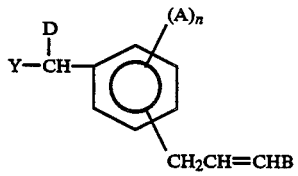

II wherein
Y represents OH;
D represents hydrogen or a cyano group;
B represents hydrogen or a methyl, ethyl or vinyl group;
A represents methyl;
n is 0, 1 or 2;
with the proviso that
(1) when the CH$_2$CH=CHB group is in the 4-position with respect to the CHDY group, the D must be hydrogen and B must be methyl, ethyl or vinyl and the configuration about the double bond in the CH=CHB group must be Z and
(2) when the group CH$_2$CH=CHB is in the 3-position with respect to the CHDY group and D is CN, then n must be 0 and
(3) when the group CH$_2$CH=CHB is in the 2 or 3-position with respect to the CHDY group, then D is CN.

2. A compound according to claim 1 wherein the —CH$_2$CH=CHB group is in the 3 or 4 position.

3. A compound according to claim 1 wherein B represent H, A represents methyl and n is 1 or 2.

4. A compound according to claim 1 wherein B represents ethyl or vinyl and the configuration at the double bond in —CH$_2$CH=CHB is Z.

5. A compound according to claim 1 wherein D represents CN and the carbon atom to which the CN group is bonded has substantially completely R or substantially completely S configuration.

6. A compound according to claim 1 which is alpha-cyano-3-(2,4-pentadienyl)benzyl alcohol or 4-(2,4-pentadienyl)benzyl alcohol or alpha-cyano-3-(2-pentenyl)-benzyl alcohol.

* * * * *